United States Patent [19]
Goodson, Jr. et al.

[11] Patent Number: 5,916,922
[45] Date of Patent: Jun. 29, 1999

[54] PHENYL GLYOXAMIDES AS SPLA2 INHIBITORS

[75] Inventors: Theodore Goodson, Jr.; Richard Waltz Harper; David Kent Herron, all of Indianapolis, Ind.

[73] Assignee: Eli Lilly and Company, Indianapolis, Ind.

[21] Appl. No.: 08/979,446

[22] Filed: Nov. 24, 1997

Related U.S. Application Data

[60] Provisional application No. 60/032,509, Dec. 3, 1996, abandoned.

[51] Int. Cl.$^6$ .................... A61K 31/165; A61K 31/055; A61K 31/19; A61K 31/255; C07C 229/00; C07C 309/24; C07C 233/00; C07F 9/38

[52] U.S. Cl. .................... 514/563; 514/114; 514/119; 514/506; 514/517; 514/538; 514/539; 514/541; 514/561; 514/562; 514/567; 514/576; 514/618; 514/621; 514/622; 558/49; 558/50; 558/60; 558/169; 558/170; 558/174; 560/9; 560/36; 560/37; 560/42; 562/15; 562/42; 562/426; 562/441; 562/442; 562/451; 562/455; 562/456; 564/162; 564/169; 564/171

[58] Field of Search ....................... 514/114, 119, 514/506, 517, 538, 539, 541, 561–563, 567, 576, 618, 621, 622; 558/49, 50, 60, 169, 170, 174; 560/9, 36, 37, 42; 562/15, 42, 426, 441, 442, 451, 455, 456; 564/162, 169, 171

[56] References Cited

U.S. PATENT DOCUMENTS

| | | | |
|---|---|---|---|
| 4,161,491 | 7/1979 | Kleemann et al. | 564/124 |
| 4,224,226 | 9/1980 | Kleemann et al. | 549/488 |
| 4,228,082 | 10/1980 | Kleemann et al. | 549/488 |
| 5,344,843 | 9/1994 | Guthrie et al. | 514/473 |
| 5,352,690 | 10/1994 | Sofia | 514/381 |

OTHER PUBLICATIONS

Geffken, D. et al., "An Improved Synthesis of N–Alkoxy–α–oxo–Arylacetamides", Synthetic Communications, vol. 26(22), pp. 4153–4156, 1996.

Ozawa, F. et al., "Palladium–Catalyzed Double Carbonylation of Aryl Halides to give α–Keto Amides. Mechanical Studies." J. Am. Chem. Soc., vol. 107, pp. 3235–3245, 1985.

Chemical Abstracts 113:114766m, 1990.

Chemical Abstracts 122:239485, 1995.

*Primary Examiner*—John Pak
*Attorney, Agent, or Firm*—Arleen Palmberg

[57] ABSTRACT

A class of novel phenyl glyoxamides is disclosed together with the use of such compounds for inhibiting sPLA$_2$ mediated release of fatty acids for treatment of conditions such as septic shock.

13 Claims, No Drawings

PHENYL GLYOXAMIDES AS SPLA2 INHIBITORS

This application claims the benefit of U.S. Provisional No. 60/032,509, filed Dec. 3, 1996 now abandoned.

This invention relates to novel substituted phenyl glyoxamides useful for inhibiting sPLA$_2$ mediated release of fatty acids for conditions such as septic shock.

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$, such as septic shock, adult respiratory distress syndrome, pancreatitis, trauma-induced shock, bronchial asthma, allergic rhinitis, rheumatoid arthritis etc.

It is desirable to develop new compounds and treatments for sPLA$_2$ induced diseases.

This invention provides compounds of the formula I

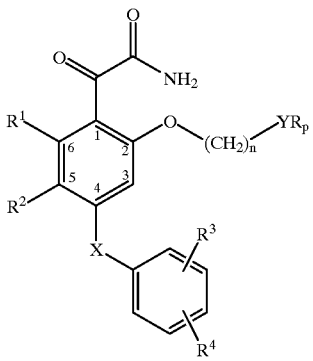

(I)

wherein:
X is —O— or —(CH$_2$)m—, where m is 0 or 1;
Y is —CO$_2$—, —PO$_3$—, —SO$_3$—;
R is independently —H or —(C$_1$-C$_4$)alkyl;
R$^1$ and R$^2$ are each independently —H, halo or —(C$_1$-C$_4$)alkyl;
R$^3$ and R$^4$ are each independently —H, —(C$_1$-C$_4$)alkyl, (C$_1$-C$_4$)alkoxy, (C$_1$-C$_4$)alkylthio, halo, phenyl or phenyl substituted with halo;
n is 1–8; and
p is 1 when Y is —CO$_2$—or —SO$_3$—and 1 or 2 when Y is —PO$_3$—;
or a pharmaceutically acceptable salt thereof.

These phenyl glyoxamides are effective in inhibiting human sPLA$_2$ mediated release of fatty acids.

The present also provides new intermediate compounds of formula II

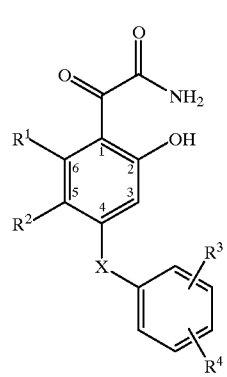

(II)

wherein:
X is —O—or —(CH$_2$)$_m$—, where m is 0 or 1;
R$^1$ and R$^2$ are each independently —H, halo or —(C$_1$-C$_4$) alkyl and
R$^3$ and R$^4$ are each independently —H, —(C$_1$-C$_4$)alkyl, —(C$_1$-C$_4$)alkoxy, (C$_1$-C$_4$)alkylthio, halo, phenyl or phenyl substituted with halo.

The compounds of formula II are useful as intermediates in preparing the compounds of formula I.

This invention is also a pharmaceutical formulation comprising a compound of formula I in association with one or more pharmaceutically acceptable diluents, carriers and excipients.

This invention is also a method of inhibiting sPLA$_2$ comprising administering to a mammal in need of such treatment a therapeutically effective amount of a compound of formula I.

According to a further aspect of the present invention, there is provided a method of selectively inhibiting sPLA$_2$ in a mammal in need of such treatment comprising administering to said mammal a therapeutically effective amount of a compound of formula I.

This invention also provides a method of alleviating the pathological effects of septic shock, adult respiratory distress syndrome, pancreatitis, trauma-induced shock, bronchial asthma, allergic rhinitis, rheumatoid arthritis, and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

Other objects, features and advantages of the present invention will become apparent from the subsequent description and the appended claims.

DETAILED DESCRIPTION OF THE INVENTION

Definitions

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl and isobutyl.

The term "halo" means chloro, fluoro, bromo or iodo.

The term "($C_1$–$C_4$) alkoxy" denotes defines a straight or branched alkyl chain having one to four carbon atoms attached to the remainder of the molecule by an oxygen atom. Typical ($C_1$–$C_4$) alkoxy groups include methoxy, ethoxy, n-propoxy, isopropoxy, n-butoxy, t-butoxy and like.

The term "($C_1$–$C_4$)alkylthio" defines a straight or branched alkyl chain having one to four carbon atoms attached to the remainder of the molecule by a sulfur atom. Typical ($C_1$–$C_4$)alkylthio groups include methylthio, ethylthio, propylthio, butylthio and the like.

The salts of the above phenyl glyoxamides are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Examples of pharmaceutically acceptable organic bases which may be used to prepare pharmaceutically acceptable salts include ammonia, amines such as triethanolamine, triethylamine, ethylamine, and the like.

PREFERRED COMPOUNDS OF THE INVENTION

Preferred substituent groups of compounds of formula (I) include the following:
(a) X is O;
(b) X is $CH_2$;
(c) Y is —$CO_2$— or —$PO_3$—;
(d) R, $R^1$ and $R^2$ are —H;
(e) $R^3$ and $R^4$ are each independently —H, —m-($C_1$–$C_4$) alkyl, -m-($C_1$–$C_4$)alkoxy, -m-halo, -m-($C_1$–$C_4$) alkylthio, or m-phenyl substituted with halo;
(f) $R^3$ is independently —H, -o-($C_1$–$C_4$)alkyl, -o-($C_1$–$C_4$) alkoxy, o-halo, -o-($C_1$–$C_4$)alkylthio, o-phenyl or o-phenyl substituted with halo;
(g) $R^3$ and $R^4$ are each independently —H or m-phenyl or -m-3-fluorophenyl;
(h) $R^3$ and $R^4$ are each independently —H, o-phenyl or -o-3-fluorophenyl; and
(i) n is 4–5.

Preferred substituent groups of compounds of formula (II) include the following:
(aa) $R^1$ and $R^2$ are —H;
(bb) $R^3$ and $R^4$ are each independently —H, -m-($C_1$–$C_4$) alkyl, -m-($C_1$–$C_4$)alkoxy, -m-halo, -m-($C_1$–$C_4$) alkylthio, or m-phenyl substituted with halo;
(cc) $R^3$ is independently —H, -o-($C_1$–$C_4$)alkyl, -o-($C_1$–$C_4$)alkoxy, -o-halo, -o-($C_1$–$C_4$)alkylthio, o-phenyl or o-phenyl substituted with halo;
(dd) $R^3$ and $R^4$ are each independently —H or m-phenyl or -m-3-fluorophenyl; and
(ee) $R^3$ and $R^4$ are each independently —H, o-phenyl or -o-3-fluorophenyl.

Further typical examples of compounds of formula I which are useful in the present invention include:

2-(6-carboxyhex-1-yloxy)-4-(3-phenylphenoxy)-5-ethylphenylglyoxamide;

Sodium 2-(8-carboxyoct-1-yloxy)-4-benzyl-5-t-butyl-6-propylphenylglyoxamide;

2-(4-carboxybut-1-yloxy)-4-(2-methoxybenzyl)-6-chlorophenylglyoxamide;

2-hydroxy-4-(2-methoxybenzyl)-6-chlorophenylgloxamide;

2-(3-carboxyprop-1-yloxy)-4-(2-ethylthio-6-fluorobenzyl)phenylglyoxamide;

Potassium 2-(4-carboxybut-1-yloxy)-4-(3,5-diphenyl)benzyl)-6-phenylglyoxamide;

2-(3-carboxyprop-1-yloxy)-4-(3-fluoro-5-phenyl)phenyl-5-propylphenylglyoxamide;

2-hydroxy-4-(3-fluoro-5-phenyl)phenyl-5-propylphenylglyoxamide;

2-(2-carboxyethoxy)-4-thiophenyl-5-fluorophenylglyoxamide;

Calcium 2-(4-carboxybut-1-yloxy)-4-(2,6-dimethyl)phenyl-phenylglyoxamide;

2-(3-carboxyprop-1-yloxy)-4-(3,5-difluorobenzyl)phenylglyoxamide;

2-(2-carboxethoxy)-4-(4-(4-chlorophenyl)benzyl)-5-bromophenylglyoxamide;

Magnesium 2-(3-carboxyprop-1-yloxy)-4-(3-ethylphenyl)-6-methylphenylglyoxamide 2-(4-carboxybut-1-yloxy)-4-(2-ethyl-6-methoxy)benzyl-5,6-dimethylphenylglyoxamide;

2-hydroxy-4-(2-ethyl-6-methoxy)benzyl-5,6-dimethylphenylglyoxamide;

2-(2-carboxyethoxy)-4-(3-methylthio-5-phenyl)benzyl-phenylglyoxamide;

2-(4-carboxybut-1-yloxy)-4-(3-propyl-5-chloro)benzyl-phenylglyoxamide;

2-(3-carboxyprop-1-yloxy)-4-(5-(3-chlorophenyl)benzyl-phenylglyoxamide;

2-(2-carboxyethoxy)-4-(3-phenyl-5-fluorobenzyl)phenylglyoxamide;

2-(3-carboxyprop-1-yloxy)-4-(4-methyl)benzyl-phenylglyoxamide;

2-(4-carboxybut-1-yloxy)-4-(2,4-dimethyl)benzyl-phenylglyoxamide;

2-hydroxy-4-(2,4-dimethyl)benzyl-phenylglyoxamide;

2-(carboxymethoxy)-4-(4-propyl)phenyl-5-methylphenylglyoxamide;

Lithium 2-(2-carboxyethoxy)-4-(3-(3-fluorophenyl)benzyl-6-butylphenylglyoxamide;

2-(3-carboxyprop-1-yloxy)-4-(3,5-diethoxy)benzyl-5-ethylphenylglyoxamide;

2-((3-dimethoxyphosphonoyl)prop-1-yloxy)-4-phenoxyphenylglyoxamide;

2-(2-phosphonoyl)ethoxy-4-benzyl-5-methyl-6-fluorophenylglyoxamide;

Sodium 2-(diethoxyphosphonoyl)methoxy-4-benzylphenylglyoxamide;

2-((3-phosphonoyl)prop-1-yloxy)-4-(2-methyl)benzylphenylglyoxamide;

2-hydroxy-4-(2-methyl)benzylphenylglyoxamide;

2-(2-dimethoxyphosphonoyl)ethoxy-4-(3,5-dichlorophenylphenyl)phenylglyoxamide;

2-((4-diethoxyphosphonoyl)but-1-yloxy)-4-(6-phenyl)phenylglyoxamide;

2-((3-phosphonoyl)prop-1-yloxy)-4-(2-fluoro-4-phenyl)phenylglyoxamide;

2-(dimethoxyphosphonoyl)methoxy-4-phenyl-5-fluoro-6-methylphenylglyoxamide;

Potassium 2-((4-phosphonoyl)but-1-yloxy)-4-(2,6-dimethoxy)phenyl-5-methylphenylglyoxamide;

2-(phosphonoyl)ethoxy-4-(4-propyl)benzyl-5-fluorophenylglyoxamide;

2-((4-diethoxyphosphonoyl)but-1-yloxy)-4-(3-(4-fluorophenyl)benzyl)-6-methylphenylglyoxamide;

2-(dimethoxyphosphonoyl)methoxy-4-(2,6-diethylbenzyl)-5-methylphenylglyoxamide;

2-(methoxysulfonyl)methoxy-4-(3,5-diethyl)benzylphenylglyoxamide;

2-sulfonylethoxy-4-(3-methylthio-5-phenyl)benzyl-phenylglyoxamide;

2-hydeoxy-4-(3-methylthio-5-phenyl)benzyl-phenylglyoxamide;

Calcium 2-((4-sulfonyl)but-1-yloxy)-4-(6-chloro)phenoxy-phenylglyoxamide;

2-((3-sulfonyl)prop-1-yloxy)-4-benzyl-phenylglyoxamide;

2-sulfonylethoxy)-4-(4-(4-fluorophenyl))benzyl-phenylglyoxamide;

2-((3-sulfony)prop-1-yloxy)-4-(4-methyl)phenoxy-phenylglyoxamide;

2-(methoxysulfonyl)methoxy-4-(2,4-dimethyl)benzyl-phenylglyoxamide;

2-(4-methoxysulfonyl)but-1-yloxy-4-(4-propyl)benzyl-5-methylphenylglyoxamide;

2-(2-ethoxysulfonyl)ethoxy-4-(3-(3-fluorophenyl)phenoxy-6-butylphenylglyoxamide;

2-hydroxy-4-(3-(3-fluorophenyl)phenoxy-6-butyiphenylglyoxamide;

Magnesium 2-((3-methoxysulfonyl)prop-1-yloxy)-4-(3,5-diethoxy)benzyl-5-ethylphenylglyoxamide;

2-((3-carboxymethoxy)prop-1-yloxy)-4-phenoxyphenylglyoxamide;

2-(2-ethoxycarbonyl)ethoxy-4-benzyl-5-methyl-6-fluorophenylglyoxamide;

2-(propoxycarbonyl)methoxy-4-benzylphenylglyoxamide;

2-((3-methoxycarbonyl)prop-1-yloxy)-4-(4-phenyl)phenoxy-phenylglyoxamide;

2-(ethoxycarbonyl)ethoxy-4-(2,6-difluorophenylphenyl)phenylglyoxamide;

2-((4-methoxycarbonyl)but-1-yloxy)-4-(3-phenyl)phenoxy-5-methylphenylglyoxamide;

2-(3-propoxycarbonyl)prop-1-yloxy-4--phenyl-6-echylphenylglyoxamide;

2-(methoxycarbonyl)methoxy-4-phenoxy-5-fluoro-6-methylphenylglyoxamide.

SYNTHESIS METHODS

Compounds where $R^1$, $R^2$, $R^3$ and $R^4$ are H, and X, Y and n and p are as defined above can be prepared according to the following Scheme I.

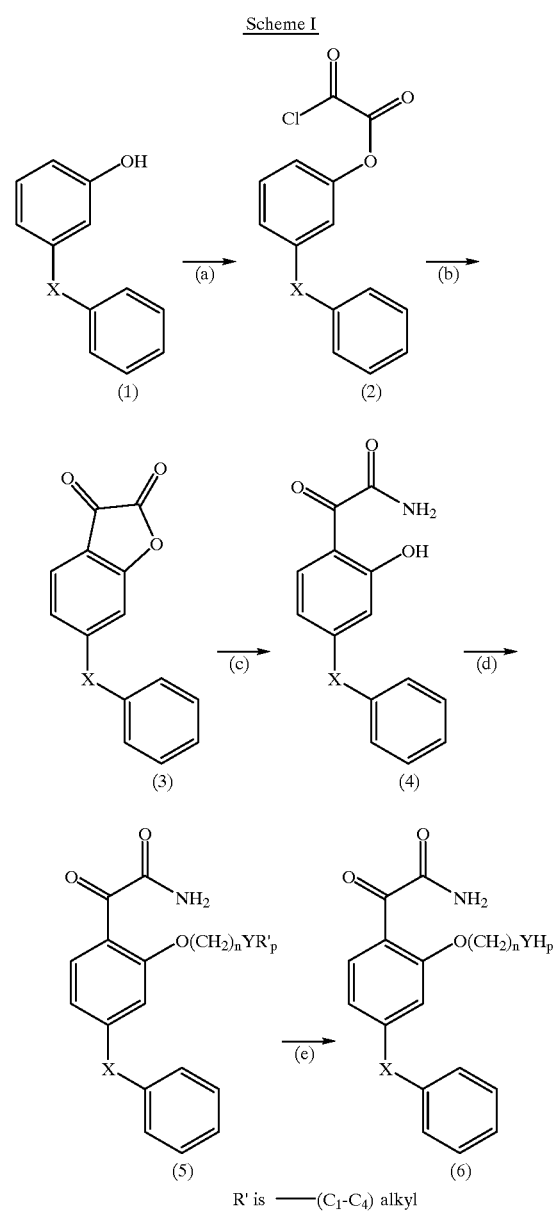

R' is ———$(C_1-C_4)$ alkyl

Reflux of (1) with oxalyl chloride in an alkyl halide solvent, such as chloroform, using 4-N,N'dimethylamino pyridine as a catalyst achieves intermediate (2).

Under Friedel-Crafts conditions, using a suitable Lewis-acid catalyst such as aluminum chloride, compound (2) is internally cyclized to form compound (3). The reaction is preferably conducted at temperatures from about 0° C. to room temperature and allowed to proceed for about 24 hours.

Aminolysis of (3) to amide (4) can be achieved by treatment with concentrated ammonium hydroxide.

Alkylation of the hydroxyl of compound (4) can be readily achieved by treatment with an appropriate alkylating agent, such as $Br(CH_2)_nY$, where Y is —$CO_2R$, —$PO_3R_2$ or $SO_3R$ and R is —$(C_1–C_4)$alkyl, to form intermediate (5). The reaction is preferably conducted in an aprotic polar solvent, such as dimethyl formamide, in the presence of potassium carbonate and a suitable catalyst, such as potassium iodide.

Conversion of (5) to the carboxylic or sulfonic acid or acid salt (6) may be achieved by treatment with an appropriate base, such as aqueous sodium hydroxide, in a polar protic solvent, such as methanol.

When n is 2, a bromoacetal must be employed as an alkylating agent to achieve the carboxylic acid (6). The alkylated moiety (5) is then converted to the acid (6) by oxidizing with sodium dichromatate in aqueous conditions.

When Y is —PO$_3$—, conversion to the acid (6), is preferably conducted in an alkyl halide solvent, such as methylene chloride, using a dealkylating agent, such as trimethylsilyl bromide, and an excess of potassium carbonate, followed by treatment with methanol.

When $R^1$, $R^2$, $R^3$ or $R^4$ are other than hydrogen, the preparation proceeds as described in Scheme II on the following page.

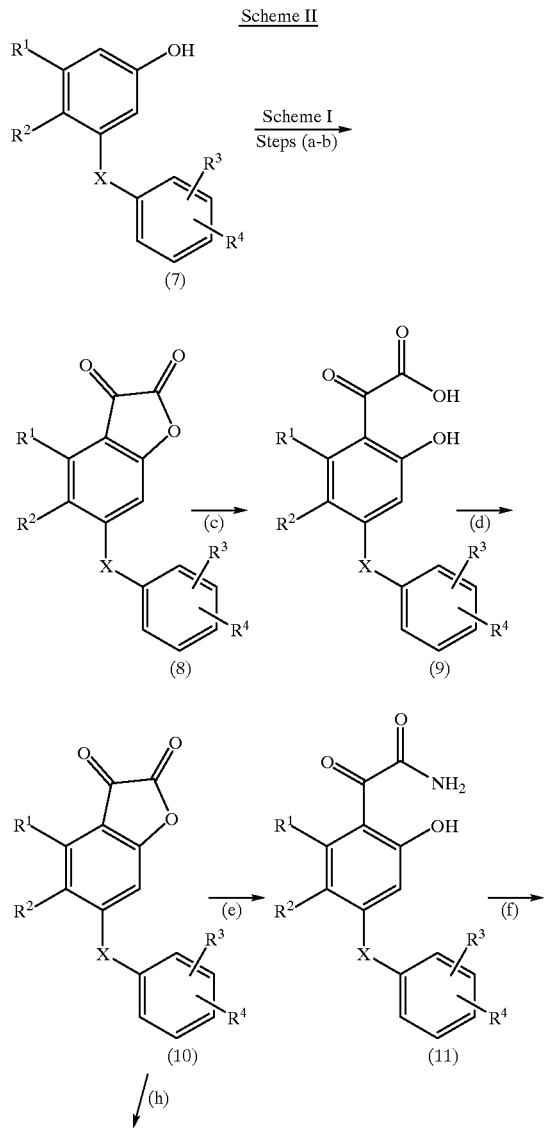

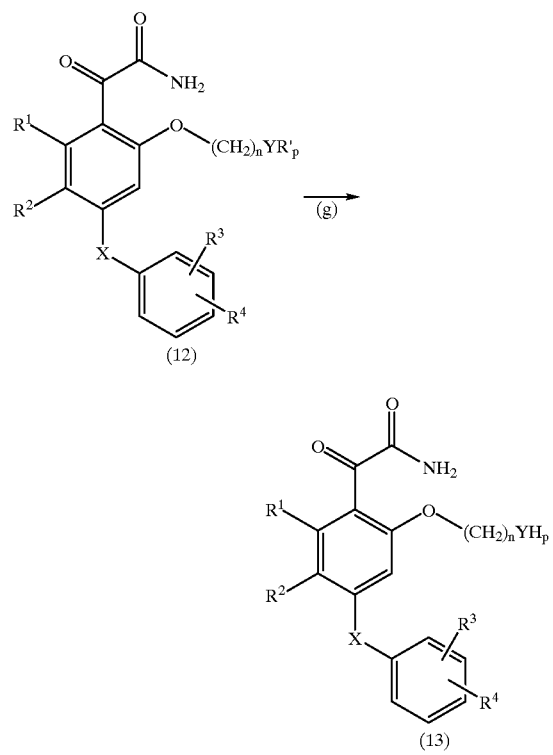

R' is as defined in Scheme I.

An appropriately $R^1$, $R^2$ substituted phenol (7) is converted to lactone (8) following the procedures described in Scheme I, steps (a–b) above.

Conversion to the intermediate (9) is accomplished by reacting (2a) with an aqueous acid, such as hydrochloric acid which affords removal of aluminum chloride from the reaction. Acid (9) is converted to the corresponding acid chloride using oxalyl chloride with dimethyl formamide as a catalyst. The acid chloride is recycled to the lactone (10) on removal of the solvent, preferably under vacuum. The lactone (10) is converted to the glyoxamide (11) by treatment with an excess of ammonia as described in Scheme I, step (c), above.

Alkylation of (11) to prepare the ester (12), followed by conversion to the acid is accomplished according to the procedure outlined in Scheme I, steps (d) and (e).

Alternately, conversion of (10) to (12) can be accomplished in a one-pot procedure by treating the lactone (10) with sodium amide in an aprotic polar solvent, such as dimethylformamide, preferably at temperatures of from about 0° C. to 20° C., followed by alkylation with an appropriate alkyl halide.

The intermediates and final products may be isolated and purified by conventional techniques, for example by concentration of the solvents, followed by washing of the residue with water, then purification by conventional techniques such as chromatography or recrystallization.

It will be readily appreciated by the skilled artisan that the starting materials are either commercially available or can be readily prepared by known techniques from commercially available starting materials. For example, when X is oxygen, starting material (1) can be readily prepared by coupling an appropriately substituted phenol with an appropriately substituted phenyl halide to prepare the anisole, under Ullmann-type conditions, by refluxing the phenol and phenyl halide in the presence of an excess of potassium carbonate and cupric oxide in an aprotic polar solvent such as pyridine. The reaction is preferably conducted under a argon blanket and is substantially complete in from 1 to 48 hours.

Demethylation of the anisole is achieved by refluxing for from 1 to 24 hours using an ether cleaving reagent, such as 40% hydrogen bromide in acetic acid, in a polar protic solvent, such as acetic acid to prepare (1).

All other reactants used to prepare the compounds in the instant invention are commercially available.

The following examples further illustrate the preparation of the compounds of this invention. The examples are illustrative only and are not intended to limit the scope of the invention in any way.

The following abbreviations are used in Examples 1 to 13 below.

HOAc is acetic acid
HBr is hydrogen bromide
EtOAc is ethyl acetate
$NaHCO_3$ is sodium bicarbonate
$Na_2SO_4$ is sodium sulfate
$CHCl_3$ is chloroform
$NH_4OH$ is ammonium hydroxide
HCl is hydrochloric acid
CuO is copper (II) oxide
$MgSO_4$ is magnesium sulfate
DAP is diammonium phosphate
$AlCl_3$ is aluminum chloride
$K_2CO_3$ is potassium carbonate
$CH_2Cl_2$ is methylene chloride
$NH_3$ is ammonia
DMF is dimethyl formamide
KI is potassium iodide
MeOH is methanol
NaH is sodium hydride
NaOH is sodium hydroxide
DMAP dimethyl amino (pyridine)

EXAMPLE 1

2-(5-carboxypent-1-yloxy)-4-phenoxyphenylglyoxamide

A. Preparation of 3-phenoxyanisole

3-Methoxyphenol (287.4 g; 2.3 Mol), 316.0 g (2.0 Mol) of bromobenzene, 552 g (4.0 Mol) of $K_2CO_3$, 12.0 g (0.19 Mol) of activated copper (prepared according to Org. Syn. Coll. Vol. II, p 445–6), Cu(II) acetate hydrate 2.0 g (11 mMol), CuO powder (2.0 g; 25 mMol), and 2.0 g of copper sulfate (13 mMol) were combined in 1500 mL of dry pyridine. The resultant mixture was heated under reflux for 3 days. After cooling, the mixture was concentrated under reduced pressure, then treated with 6N HCl. Extraction was carried out with ether. The combined organics were washed with water, dilute NaOH, and water, then concentrated under reduced pressure. The residue was distilled in vacuo to give 3-phenoxyanisole, distilling at 138–40° C./2 mm pressure, 119 g (75% yield). $H^1$ NMR (CDCl$_3$) d: 3.81 (s, 3 H), 6.61 (m, 2 H), 6.68 (d, J=7.8 Hz, 1 H), 7.06 (d, J=8.3, 2 H), 7.14 (t, J=7.4 Hz, 1 H), 7.25 (t, J=8.4 Hz, 1 H), 7.37 (t, J=7.8 Hz, 2 H).

B. Preparation of 3-phenoxyphenol

3-Phenoxyanisole (8.3 g) was added to a mixture of 50 mL of 40% HBr and 100 mL of glacial acetic acid. The resultant mixture was heated under reflux for 48 hours, then cooled and concentrated under reduced pressure. The residue was taken up in EtOAc, washed with water, saturated $NaHCO_3$, and brine. After drying with $MgSO_4$, and concentration under reduced pressure, 3-phenoxyphenol was obtained and used without further purification.

C. Preparation of 3-phenoxyphenylglyoxylic acid lactone

3-Phenoxyphenol was combined with oxalyl chloride (6.5 mL; 2 eq) and 0.1 g of DMAP (catalytic), in 30 mL of $CHCl_3$. The mixture was heated under reflux for 10 hours, then cooled and concentrated under reduced pressure. The residue was dissolved in 20 mL of dichloroethane and added dropwise at room temperature to a slurry of $AlCl_3$ in 100 mL of dichloroethane. The mixture was allowed to stir overnight at room temperature, then poured cautiously into water and allowed to stir for one hour to effect hydrolysis. Extraction was carried out with methylene chloride. The combined organics were washed with brine and dried over $MgSO_4$. After concentration under reduced pressure, the product was obtained as a yellow solid (4.1 g). A sample was recrystallized from $CH_2Cl_2$/ether for characterization. mp 137–139° C.

Elemental Analysis for $C_{14}H_8O_4$
Calculated: C 70.00, H 3.36;
Found: C 69.65, H 3.49;
M/Z 240 (M+).

D. Preparation of 2-hydroxy-4-phenoxyphenylglyoxamide

The compound of part C was combined with 30 mL of concentrated $NH_4OH$ and water, and stirred at room temperature. A homogeneous yellow solution resulted after 30 minutes. The solution was treated with concentrated HCl until a tarry residue had formed. The solution was decanted from the residue, and acidified to pH 1 by further addition of concentrated HCl. The product was collected by suction filtration and washed with fresh water. A sample was recrystallized with EtOAc/hexane for characterization. mp 144–146° C. $H^1$ NMR (CDCl$_3$) d: 5.81 (br s, 1 H), 6.42 (s, 1 H), 6.58 (d, J=10.0 Hz, 1 H), 7.06 (br s, 1 H), 7.12 (d, J=7.7 Hz, 2 H), 7.27 (m, 1 H), (t, J=7.7 Hz, 2 H), 8.68 (d, J=9.2 Hz, 1 H) M/Z 257 (M+).

E. Preparation of 2-(5-carboxypent-1-yloxy)-4-phenoxyphenylglyoxamide methyl ester 2-Hydroxy-4-phenoxyphenylglyoxamide (0.3 g; 1.2 mMol) was added to 60 mg of a 60% suspension of NaH in mineral oil in 20 mL of DMF. When gas evolution had ceased, 0.3 g of 6-methyl bromohexanate was added. The resultant solution was heated and stirred overnight while immersed in an oil bath maintained at 60–65° C. The mixture was poured into 100 mL of water and extracted with EtOAc. The combined organics were washed with brine, and dried over $MgSO_4$. The product was isolated as a white crystalline solid (0.2 g; 43% yield) by medium pressure chromatography on silica gel, eluting with EtOAc/hexane:6/4.

F. Preparation of 2-(5-carboxypent-1-yloxy)-4-phenoxyphenylglyoxamide

The ester (0.2 g; 0.52 mMol), prepared in step E, above, was combined with 1N NaOH (0.52 mL) and 5 mL of methanol in an argon atmosphere. The resultant mixture was stirred at room temperature for 7 days. The solvent was removed under reduced pressure. The residual foamy, pale, yellow solid was taken up in water. The aqueous solution was extracted with ethyl acetate, then acidified to pH 1 with concentrated HCl. The product (35 mg; 18% yield) was isolated by suction filtration and washed with fresh water.

Elemental Analysis for $C_{20}H_{21}NO_6$:
Calculated: C 64.68, H 5.70, N 3.77;
Found: C 64.50, H 5.72, N 3.65.
M/Z 371 (M+).

EXAMPLE 2

2-(3-carboxyprop-1-yloxy)-4-phenoxyphenylglyoxamide

Title compound was prepared as described in Example 1, above. 9% yield. mp 170–172° C. $H^1$ NMR (DMSO-$d_6$) d: 1.97 (m, 2 H), 2.49 (t, J=7.2 Hz, 2 H), 4.07 (t, J=6.0 Hz, 2 H), 6.60 (d, J=8.50 Hz 1 H), 6.83 (s, 1 H), 7.23 (m, 2 H), 7.33 (t, J=7.3 Hz, 1 H), 7.55 (m, 2 H), 7.64 (s, 1 H), 7.76 (d, J=8.6 Hz,1 H), 8.03 (s, 1 H), 12.18 (s, 1 H). M/Z 343 (M+).

EXAMPLE 3

2-(6-carboxyhex-1-yloxy)-4-phenoxyphenylglyoxamide

Title compound was prepared as described in Example 1, above; 69% yield. mp 132–134° C.
Elemental Analysis for $C_{21}H_{23}NO_6$
Calculated: C 65.44, H 6.02, N 3.63;
Found: C 65.63, H 6.13, N 3.39.

EXAMPLE 4

2-(7-carboxyhept-1-yloxy)-4-phenoxyphenylglyoxamide

Title compound was prepared as described in Example 1 above; 24% yield. mp 119–121° C.
Analysis for $C_{22}H_{25}NO_6$
Calculated: C 66.15, H 6.31, N 3.51;
Found: C 65.87, H 6.05, N 3.25.

EXAMPLE 5

2-(4-carboxybut-1-yloxy)-4-phenoxyphenylglyoxamide

The ester precursor of this acid was prepared by the general method outlined in Example 1, steps A–E, above. The ester (0.193 g; 0.52 mmol) was combined with 0.52 mL of 1.0N NaOH in 5 mL of methanol under an argon atmosphere. The mixture was stirred at room temperature for 7 days, then concentrated under reduced pressure to give a pale, yellow solid (0.170 g; 86% yield).
Anal Calcd for $C_{19}H_{18}NO_6Na.H_2O$:
Calculated: C 57.43, H 5.07, N 3.52;
Found: C 57.43, H 4.91, N 3.08.
$H^1$ NMR (DMSO-$d_6$)δ:1.64 (br s, 4 H), 1.90 (br t, 2 H), 3.92 (br t, 2 H), 6.50 (d, J=8.50 Hz 1 H), 6.72 (s, 1 H), 7.13 (d, J=7.3 Hz, 2 H), 7.23 (t, J=7.3 Hz, 1 H), 7.46 (t, J=7.3 Hz, 2 H), 7.76 (d, J=8.6 Hz, 1 H), 7.7–8.4 (br s, 2 H).

EXAMPLE 6

Sodium 2-carboxymethoxy-4-phenoxyphenylglyoxamide

A. Preparation of 2-carboxymethoxy-4-phenoxyphenylglyoxamide

To 25 mL of dry DMF was added 0.54 g (2 mmole) of 2-hydroxy-4-phenoxyphenylglyoxamide, the compound of Example 1, step D, above, followed by 0.244 mL (2.2 mmole) of methyl bromoacetate, 0.304 g (2.2 mmole) $K_2CO_3$, and 200 mg of dry powdered KI. The mixture was stirred 16 hours at room temperature and evaporated under vacuum. The product was redissolved in EtOAc and washed with brine. The solution was evaporated under vacuum, and the product was purified through chromatography over silica gel (30–40% EtOAc in hexane), giving 0.461 g (67%) of 2-carboxymethoxy-4-phenoxyphenylglyoxamide as an oil.
Mass Spectral Analysis (FD) m/z: 343.3 ($M^+$)

B. Preparation of sodium 2-carboxymethoxy-4-phenoxyphenylglyoxamide

Into 25 mL of MeOH was dissolved 460 mg (1.34 mmole) of the intermediate glyoxamide prepared above. To the stirred solution was added 1.34 mL of 1 N NaOH, and the hydrolysis was allowed to continue at room temperature for 24 hours. Solvent was removed under vacuum, leaving behind an oily residue, which, on addition of a few mL of EtOAc, gave 402 mg (89%) of crystalline sodium 2-carboxymethoxy-4-phenoxyphenylglyoxamide, melting at 106° C.(d).
$H^1$ NMR (DMSO-$d_6$)δ:4.12 (s, 3 H), 6.57 (d, 1 H), 7.09 (d, 2 H), 7.21 (t, 1 H), 7.43 (t, 2 H), 7.58 (d, 2 H), 8.16 (br s, 1 H)

EXAMPLE 7

2-(2-carboxy)ethoxy-4-phenoxyphenylglyoxamide

A. Preparation of 2-(1,3-dioxolan-2-yl)ethoxy-4-phenoxyphenylglyoxamide

To a stirred DMF (24 mL) solution containing 0.448 g (1.74 mmole) of 2-hydroxy-4-phenoxyphenylglyoxamide, the compound of Example 1, step D, above, was added 0.225 g (1.91 mmole) of 2-(2-bromoethyl)-1,3-dioxolane, 50 mg of dry powdered KI, and 92 mg (1.91 mmole) of NaH (50% in oil). The mixture was heated at 60° C. for 16 hours. The reaction mixture was quenched with cold brine, and the resulting organic layer was washed with cold brine twice. After drying over $Na_2SO_4$ and evaporating under vacuum, the product was purified on a preparative silica gel plate (75% EtOAc-25% hexane), giving 220 mg (35%) 2-(1,3-dioxolan-2-yl)ethoxy-4-phenoxyphenylglyoxamide as an oil.
$H^1$ NMR (CDCl$_3$) δ:2.14 (q, 2 H), 3.88–3.98 (m, 4 H), 4.12 (t, 2 H), 5.08 (t, 1 H), 5.51 (bd s, 1 H), 6.39 (bd s, 1 H), 6.57 (d, 1 H), 6.58 (s, 1 H), 7.09 (d, 1 H), 7.23 (t, 1 H), 7.42 (t, 2 H), 7.73 (d, 1 H)

B. Preparation of 2-(2-carboxyethoxy)-4-phenoxyphenylglyoxamide

In 20 ml of acetone, was dissolved 220 mg (0.62 mmole) of the intermediate dioxolanylglyoxamide prepared above. Jones oxidation reagent was dropped in until the reddish color was not extinguished. Most of the solvent was removed under vacuum, and the reaction mixture was extracted between EtOAc and cold water. The organic layer was shaken with dilute bicarbonate, and the resulting aqueous layer was acidified and extracted with EtOAc. The organic layer was dried over $Na_2SO_4$, and evaporated under vacuum. The product was redissolved in an acetone—$CH_2Cl_2$ solvent mixture (1:1), giving 15 mg (7.4%) of crystalline 2-carboxyethoxy-4-phenoxyphenylglyoxamide, melting at 140° C. (d).
Elemental Analysis for $C_{17}H_{15}NO_6$
Calculated: C, 62.01; H, 4.59; N, 4.25;
Found: C, 61.74; H, 4.64; N, 4.11.

EXAMPLE 8

2-(4-carboxybut-1-yloxy)-4-(2-phenylphenoxy) phenylglyoxamide

A. Preparation of 3-(2-phenylphenoxy)anisole

Into 200 mL of pyridine was added 26.7 g (215 mmoles) of 3-methoxyphenol, 50.0 g (215 mmoles) of 1-bromo-2-phenylbenzene, and 59.3 g (430 mmoles) of $K_2CO_3$. Under argon, the mixture was heated to 70° C., and 43.0 g (538 mmoles) powdered CuO was added. The mixture was then heated for 72 hours at reflux with vigorous stirring. After cooling and filtering, the reaction mixture was evaporated under vacuum. The residue was extracted between EtOAC and cold dilute HCl 3 times. The organic layer was dried over $Na_2SO_4$, filtered and evaporated under vacuum. The product was purified via silica gel flash chromatography (0 to 50% EtOAc in hexane), giving 50.9 g (86%) of 3-(2-phenyl)phenoxyanisole as a crystalline solid, melting at 52–54° C.

Elemental Analysis for $C_{19}H_{16}O_2$:
Calculated: C, 82.58; H, 5.84; O, 11.58:
Found: C, 82.75; H, 5.88; O, 11.40.

B. Preparation of 3-(2-phenylphenoxy)phenol

To 200 mL HOAc and 80 mL of 40% HBr was added 20 g (72.5 mmoles) of the intermediate anisole prepared above. The mixture was heated 6 hours at reflux. Most of the solvent was removed under vacuum, and the residue was shaken between EtOAc and water. The organic layer was washed with saturated $NaHCO_3$, dried over $Na_2SO_4$, and evaporated under vacuum to give 16 g (85%) of 3-(2-phenyl)phenoxyphenol as an oil, which was used without further purification.

Mass Spectral Analysis (FD) m/z: 262 (M$^+$)

C. Preparation of 2-hydroxy-4-(2-phenylphenoxy) phenylglyoxamide

To 50 mL of $CHCl_3$ was added 2.62 g (10 mmoles) of the intermediate phenol, 100 mg DAP, and 2.1 mL (22 mmoles) oxayl chloride. The mixture was heated at reflux for 16 hours. The solvent was removed under vacuum, giving the oxayl chloride condensation product as an oil, which was used without further purification.

The oxayl chloride condensation product (approx.10 mmole) was dissolved in 25 ml of 1,2-dichloroethane and added over 5 min to 3.99 g (30 mmoles) $AlCl_3$ dispersed in 25 mL 1,2-dichloroethane cooled in an ice bath. After 2 hours, the ice bath was removed, and the reaction was allowed to continue for 1 hour. The reaction was placed in an ice bath, and 50 mL concentrated $NH_4OH$ was added to it with vigorous stirring. After 1 hour, the reaction was diluted with water and filtered. The filtrate was diluted further with $CH_2CL_2$ and was shaken in a separatory funnel. The organic layer was washed with cold dilute HCL, dried over $Na_2SO_4$, and evaporated under vaccum. The product was purified over silica gel (first, a 0–100% EtOAc in hexane gradient, followed by a 20–80% MeOH in EtOAc), giving 206 mg (7.8%) 2-hydroxy-4-(2-phenyl) phenoxyphen-1-yl-glyoxamide. A crystalline analytical sample from $CH_2Cl_2$ melted at 100–103° C.

Elemental Analysis For $C_{20}H_{15}NO_4$:
Calculated: C, 72.06; H, 4.54; N, 4.20;
Found: C, 72.26; H, 4.64; N, 3.94.

Mass spectral Analysis (FD) m/z: 333 (M$^+$)

Also obtained in the latter fractions of the above mentioned chromatography was 1.14 g (34%) of 2-hydroxy-4-(2-phenyl)phenoxyphen-1-yl-glyoxylic acid as a crystalline solid, melting at 205° C. (d).

Mass Spectral Analysis (FD) m/z: 334 (M$^+$)

The glyoxylic acid was converted to the more desired glyoxamide as follows: To 25 mL of $CH_2Cl_2$ was dissolved 0.8 g (2.4 mmole) of the intermediate glyoxylic acid. The mixture was cooled by an ice bath, and then a catalytic amount of DMF was added, followed by 0.28 mL (2.9 mmole) of oxayl chloride. After 1 hour, the ice bath was rermoved, and the reaction was allowed to warm to room temperature for 1 hour. The solvent was removed under vacuum, and the the product was redissolved in 50 mL of $CH_2Cl_2$. From a lecture bottle, $NH_3$ was bubbled in over a 5 minute period with stirring. The reaction was shaken with cold dilute HCl, and the organic layer was dried over $Na_2SO_4$, and evaporated under vacuum. The crude product crystalized from $CH_2Cl_2$-hexane, giving an additonal 303 mg (38%) of 2-hydroxy-4-(2-phenyl) phenoxyphenylglyoxamide. (17%), mp=100–103° C.

Mass Spectral Analysis (FD) m/z: 333 (M$^+$)

D. Preparation of 2-(4-carboxymethoxybut-1-yloxy)-4-(2-phenyl)phenoxyphenylglyoxamide To 62.4 mg (1.3 mmole) of 50% NaH in mineral oil, which had been washed with hexane, was added 50 mL of dry DMF, 0.40 g (1.2 mmole) of 2-hydroxy-4-(2-phenyl) phenoxyphenylglyoxamide, and 100 mg of powdered dry KI and 4-methyl bromobutanate. The reaction mixture was stirred and heated 16 hours at 60° C., quenched with dilute cold HCl, and after diluting further with cold brine, it was extracted with EtOAc. The organic layer was washed with acidified brine twice, dried over $Na_2SO_4$, evaporated under vacuum. When chromatographed over silica gel (20 to 80% EtOAc in hexane), 254 mg (47%) 2-(4-carbomethoxy) butoxy-4-(2-phenyl)phenoxyphenylglyoxamide was prepared as an oil.

$H^1$ NMR (CDCl$_3$) δ:1.7–1.9 (m, 4 H), 2.39 (t, 2 H), 3.69 (s, 3 H), 3.93 (t, 2 H), 5.84 (br s, 1 H), 6.29 (br s, 1 H), 6.46 (s, 1 H), 6.49 (d, 1 H), 7.12 (d, 1 H), 7.3–7.5 (m, 8 H), 7.65 (d, 1 H);

Mass Spectral Analysis (FD) m/z: 447 (M$^+$).

E. Preparation of 2-(4-carboxybut-1-yloxy)-4-(2-phenyl) phenoxyphenylglyoxamide

Into 10 mL of MeOH was dissolved with stirring, 254 mg (0.57 mmole) of the carbomethoxy intermediate prepared above, followed by the addition of 1.14 mL 0.5 N NaOH. The mixture was stirred 16 hours at room temperature. Solvent was removed under vacuum, and the residue was diluted with water and extracted with 4:1 EtOAc: hexane. The aqueous layer was acidified with dilute HCl, and shaken with EtOAc. The organic layer was dried over $Na_2SO_4$, and evaporated under vacuum. Crystalline 2-(4-carboxy)butoxy-4-(2-phenyl)phenoxyphenylglyoxamide was obtained, 181 mg (73%), melting at M=118–20° C.

Elemental Analysis for $C_{25}H_{23}NO_6$:
Calculated: C, 68.95; H, 5.79; N, 3.23;
Found: C, 68.91; H, 5.58; N, 3.22;

$H^1$ NMR (DMSO-d$_6$) δ:1.7–1.9 (m, 4 H), 2.37 (t,2 H), 3.93 (t, 2 H), 6.32 (br s, 1 H), 6.44 (s, 1 H), 6.45 (d,1 H), 6.47 (br s, 1 H), 7.12 (d, 1 H), 7.3–7.5 (m, 8 H), 7.65 (d, 1 H)

Mass Spectral Analysis (FD) m/z: 433 (M$^+$).

EXAMPLE 9

Sodium 2-(4-carboxybut-1-yloxy)-4-phenoxy-5-methylphenyglyoxamide

A. Preparation of 3-hydroxy-4-methylanisole

To a solution of 10.0 g (65.8 mmoles) of 2-hydroxy-4-methoxybenzaldehyde in 50 mL of HOAc and 50 mL of concentrated HCl, was added 17.2 g (263.2 mg atoms) of powdered zinc. The mixture was heated one hour at 85–90° C. and then extracted three times between EtOAc and saturtated NaCl solution. The organic layer was washed with saturated $NaHCO_3$, dried over $Na_2SO_4$, and evaporated under vacuum. The crude product was purified via silica gel flash chromatography (0 to 20% EtOAc in hexane), giving 2.0 g (22.0%) of 3-hydroxy-4-methylanisole as an oil which crystallized on standing, melting at 34–35° C.

B. Preparation of 4-methyl-3-phenoxyanisole

Into 50 mL pyridine, was added 4.14 g (30 mmoles) of the hydroxyanisole prepared above, 3.48 mL (33 mmoles) of bromobenzene, and 4.8 g (60 mmoles) of $K_2CO_3$. Under argon, the mixture was heated to 70° C., and 4.8 g (60 mmoles) of powdered CuO was added. The mixture was then heated for 16 hours at reflux with vigorous stirring. Additional CuO (4.8 g,60 mmoles) and bromobenzene (3.5 mL, 60 mmoles) were added, and the reaction mixture was heated 16 hours at reflux. After cooling and filtering, the reaction mixture was evaporated under vacuum. The residue was extracted between EtOAC and cold dilute HCl three times. The organic layer was dried over $Na_2SO_4$, filtered and evaporated under vacuum. The product was purified via silica gel flash chromatography (0 to 30% EtOAc in hexane), giving 3.32 g (51.7%) 4-methyl-3-phenoxyanisole as an oil.

C. Preparation of 4-methyl-3-phenoxyphenol

To 50 mL of HOAc and 20 mL of 40% HBr was added 3.2 g (15.0 mmoles) of the intermediate methylanisole prepared above, and the mixture was heated 16 hours at reflux. Most of the solvent was removed under vacuum and the residue was shaken between EtOAc and water. The product, after drying over $MgSO_4$ and evaporating under vacuum, was purified via silica gel flash chromatography (0–30% EtOAc in hexane), giving 1.81 g (60%) 4-methyl-3-phenoxyphenol as an oil.

D. Preparation of 2-hydroxy-5-methyl-4-phenoxyphenylglyoxylic acid

To 100 mL of $CHCl_3$ was added 1.70 g (8.5 mmoles) of the intermediate methylphenol prepared above, 30 mg of DAP, and 1.79 mL (18.7 mmoles) of oxalyl chloride. The mixture was heated at reflux for 16 hours. The solvent was removed under vacuum, giving the oxalyl chloride condensation product as an oil, which was used without purification. The intermediate oxalyl chloride product was dissolved in 25 ml of 1,2-dichloroethane and added over 5 minutes to 3.39 g (25.5 mmoles) of $AlCl_3$ dispersed in 100 mL of 1,2-dichloroethane cooled in an ice bath. After 1 hour, the ice bath was removed and the reaction was allowed to continue for 30 minutes. The reaction mixture was poured into 300 mL of a 3:1 mixture of crushed ice and concentrated HCl with vigorous stirring. The organic layer was separated and washed with cold dilute HCl and dilute $K_2CO_3$. The carbonate extract was acidified with dilute HCl and extracted with EtOAc. After drying over $MgSO_4$ and evaporating under vacuum, 1.04 g (45%) of 2-hydroxy-5-methyl-4-phenoxyphenylglyoxylic acid as a crystalline solid was obtained, melting at 85–87° C.

E. Preparation of 2-hydroxy-5-methyl-4-phenoxyphenylglyoxamide

To 25 mL of $CH_2Cl_2$ containing a few drops of DMF, was added 0.80 g (4 mmoles) of the glyoxylic acid intermediate prepared above. The mixture was cooled in an ice bath, and 0.46 mL of oxalyl chloride (4.8 mmoles) was added. After 1 hour, the ice bath was removed and the reaction was allowed to continue for 1 hour. The solvent and excess oxalyl chloride were removed under vacuum, and the product was redissolved in 50 mL of $CH_2Cl_2$ and cooled in an ice bath. Approximately 5 mL of liquid $NH_3$ was added, and the reaction was stirred for 1 hour. The reaction mixture was quenched with cold concentrated HCl and, after diluting with brine and $CH_2Cl_2$, it was shaken in a separatory funnel. The organic layer was washed with brine, dried over $MgSO_4$, and concentrated, giving 225 mg (21%) of 2-hydroxy-5-methyl-4-phenoxyphenylglyoxamide, melting at 158–60° C.

Elemental Analysis for $C_{15}H_{13}NO_4$:
Calculated: C, 66.42; H, 4.83; N, 5.16;
Found: C, 66.04; H, 4.75; N, 4.82.

F. Preparation of 2-(4-carboxymethoxybut-1-yloxy)-4-phenoxy-5-methylphenylglyoxamide Compound was prepared as described in Example 8, step D, above.
Yield=47%, oil
$H^1$ NMR ($CDCl_3$) δ: 1.2–1.8 (m, 4 H), 2.23 (s, 3 H), 2.35 (t, 2 H), 3.66 (s, 3 H), 3.81 (2, 2 H), 6.11 (br s, 1 H), 6.34 (s, 1 H), 6.40 (br s, 1 H), 7.01 (d, 2 H), 7.17 (t, 1 H), 7.38 (t, 2 H), 7.64 (s, 1 H)

G. Preparation of sodium 2-(4-carboxybut-1-yloxy)-4-phenoxy-5-methylphenylglyoxamide Title compound was prepared as described in Example 8, step D, above.
Yield=70%, MP=206–9° C.
$H^1$ NMR (DMSO-d6) δ: 1.5–1.6 (m, 4 H), 1.86(t, 2 H), 2.17 (s, 4 H), 3.78 (t, 2 H), 6.52 (s, 1 H), 7.04 (d. 2 H), 7.18 (t, 1 H), 7.43 (t, 2 H), 7.64 (s, 1 H), 7.83 (br s, 1 H), 7.40 (br s, 1 H).

EXAMPLE 10

2-(3-(disodium phosphonoyl)prop1-yloxy)-4-phenoxyphenylglyoxamide

A. Preparation of 2-(3-dimethoxyphosphono)prop-1-yloxy-4-phenoxyphenylglyoxamide To 20 mL of dry DMF was added with stirring, 0.457 g (1.78 mmole) of 2-hydroxy-4-phenoxyphenylglyoxamide, 0.411 g (1.78 mmole) of (3-bromoprop-1-yl) dimethylphosphonate, 100 mg of dry powdered KI, and 57 mg (1.78 mmole) of 50% NaH dispersion in mineral oil. The mixture was heated 16 hours at 6° C., cooled, quenched with cold dilute HCl, and shaken between EtOAc and brine. The organic layer was washed with brine twice, dried over $Na_2SO_4$, and evaporated under vacuum. The product was chromatographed over silica gel (0 to 100% EtOAc in hexane), giving 0.353 g (49%) 2-(3-dimethoxyphosphonoyl) prop-1-yloxy-4-phenoxyphenylglyoxamide as an oil.

Elemental Analysis for $C_{19} H_{22} N O_7$:
Calculated: C, 56.02; H, 5.73: N, 2.67;
Found: C, 56.02; H, 5.44; N, 2.67;
$H^1$ NMR (CDCl3) δ: 2.0–2.2 (m, 4 H), 3.77 (s, 3 H), 3.81 (s, 3 H), 4.00 (t,2 H), 6.25 (br s, 1 H), 6.56 (s, 1 H), 6.59 (d, 1 H), 7.09 (d, 2 H), 7.23 (t, 1 H),7.40 (t, 2 H), 7.78 (d, 1 H); Mass Spectral Analysis (FD) m/z: 407.

B. Preparation of 2-(3-(disodium phosphonoyl)prop-1-yloxy)-4-phenoxyphenylglyoxamide Into 10 mL of $CH_2Cl_2$, was added 0.35 g of intermediate dimethylphosphonate prepared above, 0.95 g (6.88 mmole) of $K_2CO_3$, and 0.91 mL (6.88 mmole) of trimethylsilyl bromide. The reaction mixture was stirred 16 hours at room temperature. The reaction mixture was evaporated under vacuum, and treated with 15 mL of MeOH at room temperature for 1 hour. The mixture was filtered and diluted with EtOAc to give a solid, which was chromatographed on an ionization column (5–30% acetonitrile in water). Fractions were lyophilized, giving 140 mg (43%) of 2-(3-disodium phosphonoyl)prop-1-yloxy-4-phenoxyphenylglyoxamide as a solid.

$H^1$ NMR (DMSO-$d_6$) δ: 1.73 (m, 2 H), 2.17 (m, 2 H), 4.10 (t, 2 H), 6.63 (d, 1 H), 6.75 (s, 1 H), 7.19 (d, 2 H), 7.32 (t, 1 H), 7.53 (t, 2 H), 7.84 (d, 1 H).

EXAMPLE 11

2-(4-carboxybut-1-yloxy)-4-(3-phenylphenoxy)phenylglyoxamide

A. Preparation of 3-(3-phenylphenoxy)anisole

Under the Ullmann conditions used in Example 8, steps A and B, above, 13.3 g of 3-methoxyphenol (107 mmole) was condensed with 1-bromo-3-phenylbenzene, giving, after purifying over silica gel, (0–30% EtOAc in hexane gradient) 17.8 g (60%) of 3-(3-phenylphenoxy)anisole as a crystalline solid, melting at 41–42° C.

Mass Spectral Analysis (FD) m/z: 276 ($M^+$)

B. Preparation of 3-(3-phenylphenoxy)phenol

The anisole derivative prepared above (17.7 g, 64 mmole) was demethylated in HOAc/40% HBr under the conditions of Example 8, step C, above and, after purifying the product over silica gel, (0–30% EtOAc in hexane gradient), 12.2 g (72%) of 3-(3-phenylphenoxy)phenol as an oil was obtained.

Elemental Analysis for $C_{18} H_{14} O_2$:
Calculated: C, 82.42; H, 5.38; O, 12.20;
Found: C, 82.17; H, 5.38; O, 12.42;

C. Preparation of 2-hydroxy-4-(3-phenylphenoxy)phenylglyoxylic acid

As in Example 8, step D, above, the intermediate phenol prepared above (7.4 g, 31.4 mmole) was treated with oxalyl chloride, and after removing solvent, the product was subjected to $AlCl_3$. The reaction mixture was quenched by pouring it into 1 L of 2:1 mixture of crushed ice and concentrated HCl with vigorous stirring. The organic layer was separated, washed with brine, diluted with EtOAc to achieve a clear solution, and dried over $MgSO_4$. The product was concentrated under vacuum and purified by chromatography over silica gel (0–100% EtOAc in hexane then 0–20% MeOH in EtOAc), giving 4.3 g (42%) 2-hydroxy-4-(3-phenylphenoxy)phenylglyoxylic acid as an oil.

Mass Spectral Analysis (FD) m/z: 334 ($M^+$)

D. Preparation of 2-hydroxy-4-(3-phenylphenoxy)phenylglyoxylic acid lactone

Into 150 mL of $CH_2Cl_2$ was dissolved 4.3 g (12.9 mmole) of the glyoxylic acid prepared above. After adding 10 drops of DMF and cooling the mixture with an ice bath, 1.48 mL of oxalyl chloride (15.5 mmole) was added to the stirred mixture in one portion. After 30 minutes the ice bath was removed, and the reaction was allowed to continue for 1 hour. The reaction mixture was concentrated under vacuum and a solid formed, which was washed with 1:1 $CH_2Cl_2$:hexane, giving 3.5 g 2-hydroxy-4-(3-phenylphenoxy)phenylglyoxylic acid lactone, melting at 55–58° C.

Mass Spectral Analysis (FD) m/z: 316 ($M^+$)

E. Preparation of 2-(4-carboxymethoxybut-1-yloxy)-4-(3-phenylphenoxy)phenylglyoxamide To 50 mL of dry DMF, was added 1.58 g (5 mmole) of 2-hydroxy-4-(3-phenylphenoxy)phenylglyoxylic acid lactone with stirring. The solution was cooled with an ice bath and 0.234 g (6.0 mmole) of sodium amide was added. After 15 minutes, 0.786 mL (5.5 mmole) of methyl 5-bromovalerate was added, and the ice bath was removed, allowing the mixture to attain room temperature. The mixture was heated 16 hours at 60° C. and then quenched with cold dilute HCl. The reaction mixture was shaken between EtOAc and cold dilute HCl. The organic layer was washed with cold dilute HCl twice, dried over $Na_2SO_4$, and concentrated under vacuum. Product was chromatographed over silica gel (0 to 70% EtOAc in hexane), giving 0.682 g (31%) 2-(4-carbomethoxybut-1-yloxy)-4-(3-phenylphenoxy)phenylglyoxamide as an oil.

$H^1$ NMR ($CDCl_3$) δ: 1.8–1.9 (m, 4 H), 2.40 (t, 2 H), 3.6(s, 3 H), 4.00 (t, 2 H), 5.77 (br s, 1 H), 6.30 (br s, 1 H), 6.60 (s, 1 H), 6.61 (d, 1 H), 7.06 (br s, 1 H) 7.3–7.5 (m, 6 H), 7.59 (d, 2 H), 7.74 (d, 1 H).

F. Preparation of 2-(4-carboxybut-1-yloxy)-4-(3-phenyl)phenoxyphenylglyoxamide

Into 20 mL of MeOH was dissolved at room temperature, 0.682 g (1.53 mmole) of the glyoxamide intermediate prepared above. To the solution was added 3.05 mL of 0.5 N NaOH. After stirring for 15 hours, the solvent was removed under vacuum, and the residue was diluted with water and extracted with EtOAc. Crystals were filtered from the organic layer, giving 0.458 g (69%) of 2-(4-carboxy)butoxy-4-(3-phenyl)phenoxyphenylglyoxamide, melting at 97–98° C.

$H^1$ NMR ($CDCl_3$)δ: 1.6–1.8 (m, 4 H), 2.28 (t, 2 H), 4.02 (t, 2 H), 6.61 (d, 1 H), 6.86 (s, 1 H), 7.15 (br s, 1 H), 7.4–7.6 (m, 7 H), 7.70 (d, 3 H), 7.94 (br s, 1 H), 12.02 (br s, 1 H);

Mass Spectral Analysis (FD) m/z: 433 ($M^+$).

EXAMPLE 12

2-(4-carboxypent-1-yloxy)-4-(2-phenylphenoxy)phenylglyoxamide

A. Preparation of 2-(4-carbomethoxypent-1-yloxy)-4-(2-phenylphenoxy)phenylglyoxamide Compound was prepared as described in Example 8, steps A–D, above.

Yield=63%, MP=70–74° C.

Elemental Analysis for $C_{27} H_{27} N O_6$:
Calculated: C, 70.27; H, 5.90; N, 3.04;
Found: C, 72.26; H, 6.31; N, 2.95;

Mass Spectral Analysis (FD) m/z: 461 ($M^+$).

B. Preparation of 2-(4-carboxy)pentoxy-4-(2-phenyl)phenoxyphenylglyoxamide

Title compound was prepared as described in Example 8, step E above.

Yield=42%, MP=97–99° C.

Elemental Analysis for $C_{26} H_{25} N O_6$:
Calculated: C, 69.79; H, 5.53; N, 3.13;
Found: C, 69.57; H, 5.62; N, 3.06;

$H^1$ NMR ($DMSOd_6$)δ: 1.39 (quin, 2 H), 1.48 (quint, 2 H), 1.63 (quint, 2 H), 2.21 (t, 2 H), 3.88(t, 2 H), 6.41 (d,1 H), 6.63 (s, 1 H), 7.17 (d, 1 H), 7.3–7.6 (m, 8 H), 7.88 (s, 1 H);

Mass Spectral Analysis (FD) m/z: 447 ($M^+$).

EXAMPLE 13

2-(4-carboxybut-1-yloxy)-4-phenylphenylglyoxamide

A. Preparation of 2-hydroxy-4-phenylphenylglyoxylic acid lactone

Commercially available 3-phenylphenol was treated with oxalyl chloride, and the resulting product was treated with $AlCl_3$ as described in Example 1, step C, above. After quenching the reaction mixture from the $AlCl_3$ treatment with water, it was dried over $MgSO_4$ and concentrated, giving crystalline 2-hydroxy-4-phenylphenylglyoxylic acid lactone (85%), melting at 131–33° C.

Mass Spectral Analysis (FD) m/z: 224 ($M^+$)

B. Preparation of 2-hydroxy-4-phenylphenylglyoxamide

The lactone prepared above, (4.0 g, 17.9 mmole), was dissolved in 200 mL of $CH_2Cl_2$ and excess gaseous ammonia was bubbled in over 5 minutes. The reaction mixture was shaken with brine, dried over $MgSO_4$, and concentrated. On cooling, the product crystallized, giving 2-hydroxy-4-phenylphenylglyoxamide (93%), with a mp of 150° C. (d).

Elemental Analysis for $C_{14} H_{11} O_3$:

Calculated: C, 69.70; H, 4.60; N, 5.81;
Found: C, 69.72; H, 4.59; N, 5.57.
Mass Spectral Analysis (FD) m/z: 241 (M$^+$)

C. Preparation of 2-(4-carboxymethoxybut-1-yloxy)-4-phenylphenylglyoxamide

Compound was prepared as described in Example 8, step D, above.
Yield=28%, MP=119–20° C.
H$^1$ NMR (DMSOd$_6$)δ: 1.6–1.8 (m, 4 H), 2.39 (t, 2 H), 3.58 (s, 3 H), 4.18 (t,2 H), 7.36 (d, 1 H), 7.38 (s, 1 H), 7.4–7.5 (m, 3 H), 7.58 (s, 1 H), 7.70 (d, 1 H), 7.38 (d, 2 H), 8.00 (s, 1 H);
Mass Spectral Analysis (FD) m/z: 355 (M$^+$)

D. Preparation of 2-[(4-carboxybut-1-yloxy]-4-phenylphenylglyoxamide

Title compound was prepared as described in Example 8, step E, above.
Yield=58%, MP=157–158° C.
Elemental Analysis for C$_{19}$ H$_{19}$N O$_5$:
Calculated: C, 66.85; H, 5.61; N, 4.10;
Found: C, 66.81; H, 5.59; N, 4.14;
H$^1$ NMR (DMSOd$_6$)δ: 1.6–1.8 (m, 4 H), 2.32 (t, 2 H), 4.14 (t, 2 H), 7.36 (d, 1 H), 7.39 (s, 1 H), 7.4–7.5 (m, 3 H), 7.56 (s, 1 H), 7.71 (d, 1 H), 7.78 (d, tH), 8.00 (s, 1 H), 12.02 (s, 1 H);
Mass Spectral Analysis (FD) m/z: 341 (M$^+$).

Therapeutic Use of Phenyl Glyoxamides

The phenyl glyoxamide compounds described herein are believed to achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenases, cyclooxygenases, etc.

The method of the invention for inhibiting sPLA$_2$ mediated release of fatty acids comprises contacting sPLA$_2$ with a therapeutically effective amount of the compound of Formula (I), or salts thereof.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administering to the mammal a compound of formula (I) in a therapeutically effective amount. A "therapeutically effective" amount is an amount sufficient to inhibit sPLA$_2$ mediated release of fatty acid and to thereby inhibit or prevent the arachidonic acid cascade and its deleterious products. The therapeutic amount of compound of the invention needed to inhibit sPLA$_2$ may be readily determined by taking a sample of body fluid and assaying it for sPLA$_2$ content by conventional methods.

Pharmaceutical Formulations of the Invention

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

Pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the phenyl glyoxamide compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or a pharmaceutically acceptable salt, solvate, or prodrug thereof.

FORMULATION 1

Hard gelatin capsules are prepared using the following ingredients:

|  | Quantity (mg/capsule) |
| --- | --- |
| 2-(6-carboxyhex-1-yloxy)-4-phenoxyphenyl-5-ethylphenylglyoxamide | 250 |
| Starch, dried | 200 |
| Magnesium stearate | 10 |
| Total | 460 mg |

FORMULATION 2

A tablet is prepared using the ingredients below:

|  | Quantity (mg/tablet) |
| --- | --- |
| 2-(4-carboxybut-1-yloxy)-4-(3,5-diphenyl)phenyl)-6-methylphenylglyoxamide | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight |
| --- | --- |
| 2-(2-carboxyethoxy)-4-(3-(3-fluorophenyl)benzyl-6-butylphenylglyoxamide | 0.25 |
| Ethanol | 25.75 |
| Propellant 22 | 74.00 |
| (Chlorodifluoromethane) |  |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULTAION 4

Tablets, each containing 60 mg of active ingredient, are made as follows:

| 2-(diethoxyphosphonoyl)methoxy-4-benzylphenylglyoxamide | 60 | mg |
| --- | --- | --- |
| Starch | 45 | mg |
| Microcrystalline cellulose | 35 | mg |
| Polyvinylpyrrolidone (as 10% solution in water) | 4 | mg |
| Sodium carboxymethyl starch | 4.5 | mg |
| Magnesium stearate | 0.5 | mg |
| Talc | 1 | mg |
| Total | 150 | mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| 2-(4-phosphonoylbut-1-yloxy)-4-(2,6-dimethoxy)phenylphenylglyoxamide | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| | |
|---|---|
| 2-(4-methoxysulfonylbut-1-yloxy)-4-(4-propyl)benzyl-5-methylphenylglyoxamide | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| | |
|---|---|
| 2-(3-methoxycarbonylprop-1-yloxy)-4-(4-phenyl)benzylphenylglyoxamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | |
|---|---|
| 2-carbomethoxymethoxy-4-phenyl-5-fluoro-6-methylphenylglyoxamide | 100 mg |
| Isotonic saline | 1,000 ml |

The solution of the above ingredients generally is administered intravenously to a subject at a rate of 1 ml per minute.

ASSAY EXPERIMENTS

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A. Dennis, *Analytical Biochemistry*, 204, pp. 190–197, 1992 (the disclosure of which is incorporated herein by reference):

Reagents:
  REACTION BUFFER -
    $CaCl_2.2H_2O$ (1.47 g/L)
    KCl (7.455 g/L)
    Bovine Serum Albumin (fatty acid free) (1 g/L)
    (Sigma A-7030, product of Sigma Chemical Co. St. Louis Mo., USA)
    TRIS HCl (3.94 g/L)
    pH 7.5 (adjust with NaOH)
  ENZYME BUFFER -
    0.05 $NaOAc.3H_2O$, pH 4.5
    0.2 NaCl
    Adjust pH to 4.5 with acetic acid
  DTNB -5,5'-dithiobis-2-nitrobenzoic acid
  RACEMIC DIHEPTANOYL THIO—PC
    racemic 1,2-bis(heptanoylthio)-1,2-dideoxy-sn-glycero-3-phosphorylcholine
    TRITON X-100™ prepare at 6.249 mg/ml in reaction buffer to equal 10 uM.
    TRITON X-100™ is a polyoxyethylene non-ionic detergent supplied by Pierce Chemical Company 3747 N. Meridian Road Rockford, Ill. 61101
  REACTION MIXTURE -
    A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.
    The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure
  1. Add 0.2 ml reaction mixture to all wells;
  2. Add 10 ul test compound (or solvent blank) to appropriate wells, mix 20 seconds;
  3. Add 50 nanograms of $sPLA_2$ (10 microliters) to appropriate wells;
  4. Incubate plate at 40° C. for 30 minutes;
  5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Compounds of the instant invention were tested in Assay Example 1 and were found to be effective.

ASSAY EXAMPLE 2

Method

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, product of Grass Medical Instruments Co., Quincy, Ma., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative concentration-response curves

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.). Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of $sPLA_2$, the compounds and their respective vehicles were added to the tissues 30 minutes prior to starting the $sPLA_2$ concentration-response curves.

Statistical analysis

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the $ED_{50}$ for the control curve, the steepness of the curves, and the $pA_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA2 may be interpreted as the apparent $K_B$, the dissociation constant of the inhibitor.

To estimate the drug-induced suppression of the maximal responses, $sPLA_2$ responses (10 ug/ml) were determined in the absence and presence of drug, and percent suppression was calculated for each pair of tissues. Representative examples of inhibitory activities are presented in Table 2, below.

Ref. 1 - van, J. M.: Cumulative dose-response curves. II. Technique for the making of dose-response curves in isolated organs and the evaluation of drug parameters. *Arch. Int. Pharmacodyn. Ther.*, 143: 299–330, 1963.

Ref. 2 - Waud, D.: Analysis of dose-response relationships. in *Advances in General and Cellular Pharmacology* eds Narahashi, Bianchi 1:145–178, 1976.

Compounds of the instant invention were tested in Assay Example 2 and were found to be effective.

We claim:

1. A compound of the formula (I)

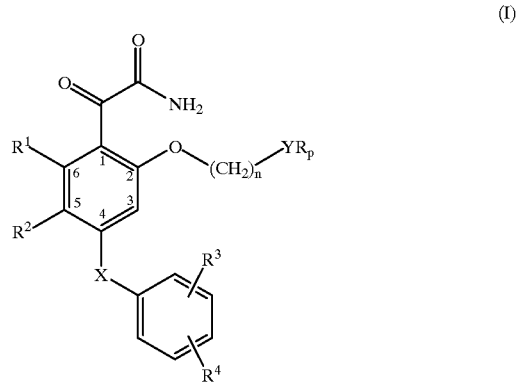

wherein:

X is —O— or —$(CH_2)_m$—, where m is 0 or 1;

Y is —$CO_2$—, —$PO_3$—, —$SO_3$—;

R is independently —H or —$(C_1-C_4)$alkyl;

$R^1$ and $R^2$ are each independently —H, halo or —$(C_1-C_4)$ alkyl;

$R^3$ and $R^4$ are each independently —H, —$(C_1-C_4)$alkyl, $(C_1-C_4)$alkoxy, $(C_1-C_4)$alkylthio, halo, phenyl or phenyl substituted with halo;

n is 1–8; and p is 1 when Y is —$CO_2$— or —$SO_3$—and 1 or 2 when Y is —$PO_3$—;

or a pharmaceutically acceptable salt thereof.

2. A compound of formula I as claimed in claim 1 wherein X is oxygen, Y is —$CO_2$—, n is 4–5, R, $R^1$, $R^2$ and $R^3$ are —H, and $R^4$ is phenyl or phenyl substituted with halo.

3. A compound of formula I as claimed in claim 1 which is 2-(4-carboxybut-1-yl-oxy)-4-(3-phenylphenoxy) phenylglyoxamide.

4. A pharmaceutical formulation comprising a compound of formula I as claimed in claim 1 together with a pharmaceutically acceptable carrier or diluent therefor.

5. A method of inhibiting $sPLA_2$ in a mammal in need of $sPLA_2$ inhibition comprising administering to said mammal a pharmaceutically effective amount of a compound of formula I as claimed in claim 1.

6. A method of claim 5 wherein the compound is 2-(4-carboxybut-1-yl-oxy)-4-(3-phenylphenoxy) phenylglyoxamide.

7. A method of selectively inhibiting sPLA₂ in a mammal in need of selective sPLA₂ inhibition comprising administering to said mammal a pharmaceutically effective amount of a compound of formula I as claimed in claim 1.

8. A method of claim 7 wherein the mammal is a human.

9. A method of claim 8 wherein the compound is 2-(4-carboxybut-1-yl-oxy)-4-(3-phenylphenoxy)phenylglyoxamide.

10. A method of claim 5 of alleviating the pathological effects of septic shock, adult respiratory distress syndrome, pancreatitis, trauma-induced shock, bronchial asthma, allergic rhinitis, and rheumatoid arthritis which comprises administering to a mammal in need of alleviation of said pathological effects a compound of formula I as claimed in claim 1 in an amount sufficient to inhibit sPLA₂ mediated release of fatty acid and to thereby inhibit the arachidonic acid cascade and its deleterious products.

11. A method of claim 10 wherein the mammal is a human.

12. A method of claim 11 wherein the compound is 2-(4-carboxybut-1-yl-oxy)-4-(3-phenylphenoxy)phenylglyoxamide.

13. A compound of the formula II

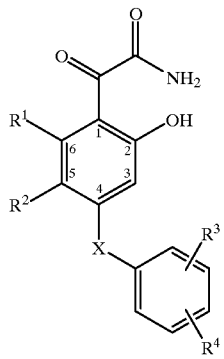

(II)

wherein:
X is —O— or —(CH$_2$)$_m$—, where m is 0 or 1;
R$^1$ and R$^2$ are each independently —H, halo or —(C$_1$–C$_4$)alkyl and
R$^3$ and R$^4$ are each independently —H, —(C$_1$–C$_4$)alkyl, —(C$_1$–C$_4$)alkoxy, (C$_1$–C$_4$)alkylthio, halo, phenyl or phenyl substituted with halo.

* * * * *